United States Patent [19]

Kan et al.

[11] Patent Number: 4,957,860
[45] Date of Patent: Sep. 18, 1990

[54] METHOD FOR PRODUCING OLIGOSACCHARIDE

[75] Inventors: Tatsuhiko Kan; Yoichi Kobayashi, both of Tokyo, Japan

[73] Assignee: Kabushiki Kaisha Yakult Honsha, Tokyo, Japan

[21] Appl. No.: 112,068

[22] Filed: Oct. 26, 1987

[30] Foreign Application Priority Data

Oct. 27, 1986 [JP] Japan ............................. 61-253857

[51] Int. Cl.$^5$ ................ C12P 19/04; C12N 9/38; C12N 1/14; C07H 3/00
[52] U.S. Cl. ................ 435/101; 435/207; 435/254; 435/911; 435/913; 435/918; 536/1.1; 536/123; 536/124
[58] Field of Search .............. 435/101, 918, 913, 911, 435/254, 207; 536/124, 123, 1.1

[56] References Cited

U.S. PATENT DOCUMENTS 3,592,739  7/1971  Sternberg ..................... 435/918
3,919,049  11/1975  Kiuchi et al. .................. 435/918
4,435,389  3/1984  Mutai et al. ................... 435/244

FOREIGN PATENT DOCUMENTS 237075  10/1986  Japan ........................... 435/918
87/05936  10/1987  World Int. Prop. O.

OTHER PUBLICATIONS

*Chemical Abstracts*, Nakano et al., Nov. 23, 1987, p. 365, #193924(p).
M. Dixon et al.: "Enzymes", 2nd Edition, 1971, pp. 36, 37, 144–151, 466, 467, Longman, London, GB pp. 27, 148, 467.

Primary Examiner—Ronald W. Griffin
Assistant Examiner—Pamela S. Webber
Attorney, Agent, or Firm—Oblon, Spivak, McClelland, Maier & Neustadt

[57] ABSTRACT

The present invention provides a method of producing oligosaccharides by the reaction between lactose and β-galactosidase from aspergillus oryzae in which an concentration of lactose in an enzyme reaction mixture is between 50 and 90% (w/v) and a reaction temperature is within the range of 55° C. to the temperature at which the β-galactosidase in the reaction mixture is inactivated. This invention therefore makes it possible to obtain the sugar mixture containing high-purity oligosaccharides, small amounts of unreacted lactose and by produced monosaccharides.

5 Claims, 3 Drawing Sheets

METHOD FOR PRODUCING OLIGOSACCHARIDE

BACKGROUND OF THE INVENTION

The present invention relates to a method for producing oligosaccharides which are growth factors for bifidobacteria in vivo.

In particular, the present invention has been achieved with a view to obtaining high-purity oligosaccharides containing less unreacted lactose and by produced monosaccharides, such as galactose and glucose, in a production of oligosaccharides by reacting lactose with β-galactosidase from *Aspergillus oryzae*.

Oligosaccharides expressed by the formula Gal—(-Gal)$_n$—Glc (wherein Gal denotes a galactose residue; Glc, a glucose residue; and n, an integer of 1 to 4) (simply referred to as "oligosaccharides" hereinafter) are major components of oligosaccharides in breast milk, and are useful as growth factors for bifidobacteria which are useful bacteria in the human intestines.

In the method of "oligosaccharides" production, it is a typical method that lactose is reacted with β-galactosidase from *Aspergillus oryzae* (published in Japanese Patent Publication No. 58-20266). In this method, the following condition is recommended: reaction temperature of 20° to 50° C., a concentration of lactose of about 10 to 50%, a pH of 3 to 8, and a concentration of enzyme of 1 to 100 units/ml. The above-described upper limit of the concentration of lactose is related to the optimum temperature of β-galactosidase from *Aspergillus oryzae*. Because, lactose is difficult to dissolve much in water, so only about 50% of it can be dissolved in water within the range of optimum temperatures of the β-galactosidase from *Aspergillus oryzae*.

The above-described method of producing "oligosaccharides" which uses β-galactosidase from Aspergillus oryzae is excellent in view of the fact that it can provide a higher yield of oligosaccharides than methods using β-galactosidase from other microorganisms. But it has a problem in that the maximum ratio of the conversion of lactose into "oligosaccharides" is only about 27%. In addition, it is difficult to separate the "oligosaccharides" from the reaction product which contain large amounts of unreacted lactose and by produced monosaccharides such as galactose and glucose. Therefore, when using "oligosaccharides" the above-described reaction products are normally used as they are. As a result, unnecessary lactose and monosaccharides are often used together with the "oligosaccharides", resulting in the problems that foods and drinks containing the "oligosaccharides" have high calorie levels and are difficult for patients with lactose intolerance to uptake. Therefore, there has been a disadvantage in that the usable range and usages of such products are limited.

The above-described method also has a following problem. Since the sugar(s) concentration of the reaction solution is low, it is necessary to concentrate for preventing contamination with bacteria and reducing the product transportation costs, and thus large heat-energy costs and equipment costs are necessary.

It is an object of the present invention to improve the above-described old method of producing "oligosaccharides" using β-galactosidase.

SUMMARY OF THE INVENTION

It is an object of the present invention to obtain the reaction product containing high-purity "oligosaccharides" and small amounts of unreacted lactose and by produced monosaccharides, such as galactose and glucose, in the production of "oligosaccharides" by reacting lactose with β-galactosidase from *Aspertillus oryzae*.

In particular, it is an object of the present invention to provide a method of producing "oligosaccharides" in a production of oligosaccharides expressed by the formula Gal—(Gal)$_n$—Glc (wherein Gal denotes a galactose residue; Glc, a glucose residue; and n, an integer of 1 to 4) by reacting lactose with β-galactosidase from *Aspergillus oryzae*, characterized in that lactose concentration of the reaction mixture is 50 to 90% (w/v) and a reaction temperature is within a range from 55° C. to the temperature at which β-galactosidase is inactivated in the reaction solution.

DETAILED DESCRIPTION OF THE INVENTION

The method adopted by the present invention is characterized in that lactose concentration in reaction mixture is 50 to 90% (w/v) and a reaction temperature is within a range from 55° C. to the temperature lower than an inactivation temperature of β-galactosidase in the reaction mixture, when the oligosaccharides production is done by reacting lactose with β-galactosidase from *Aspergillus oryzae*.

This method is based on a new finding that β-galactosidase from *Aspergillus oryzae* is possible to convert lactose into oligosaccharides without inactivating in a high-concentration lactose solution, even at a temperature which is higher than usual inactivating temperatures for this enzyme. In other words, by using this property of β-galactosidase, it is able to react at high temperature and with high lactose concentration in reactive mixture. Therefore it enables to prevent crystallization of lactose.

Figure 1:
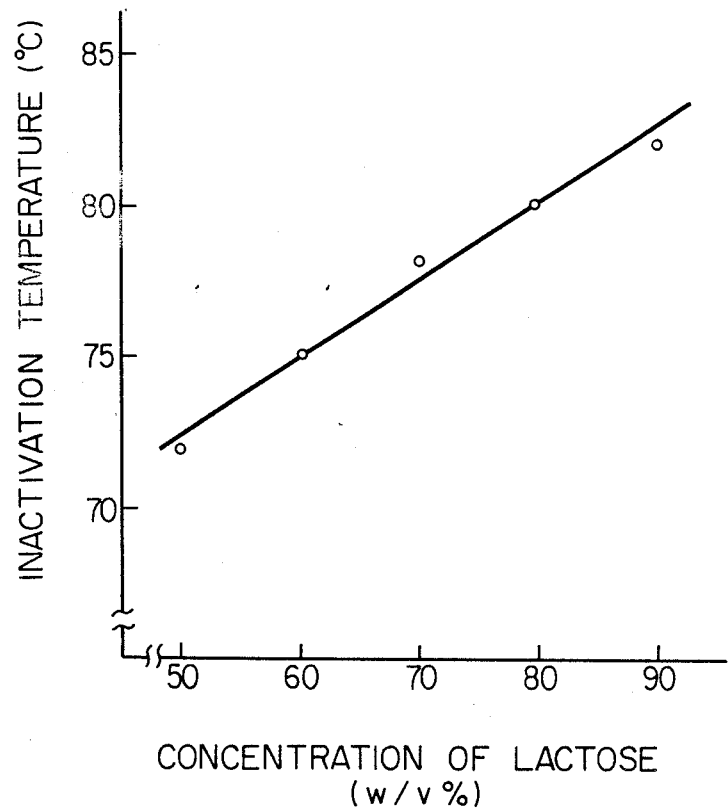
FIG. 1 shows the relationship between lactose concentration and the inactivation temperature of β-galactosidase.

FIG. 1 shows the inactivation temperatures of β-galactosidase from *Aspergillus oryzae* in lactose solutions. It can be seen from this figure that the inactivation temperature increases substantially in proportion to the concentration of lactose. Therefore, the higher the concentration of lactose, the more the reaction temperature can be increased. Lactose content can be in a range between 50–90% (w/v), preferably 60–85%, most preferably 70–80%. Reaction temperature is, generally, within a range of 55°–83° C. Depending on the lactose content, 60°–80° C. is preferable and 62°–75° C. is most preferable.

Figure 2:
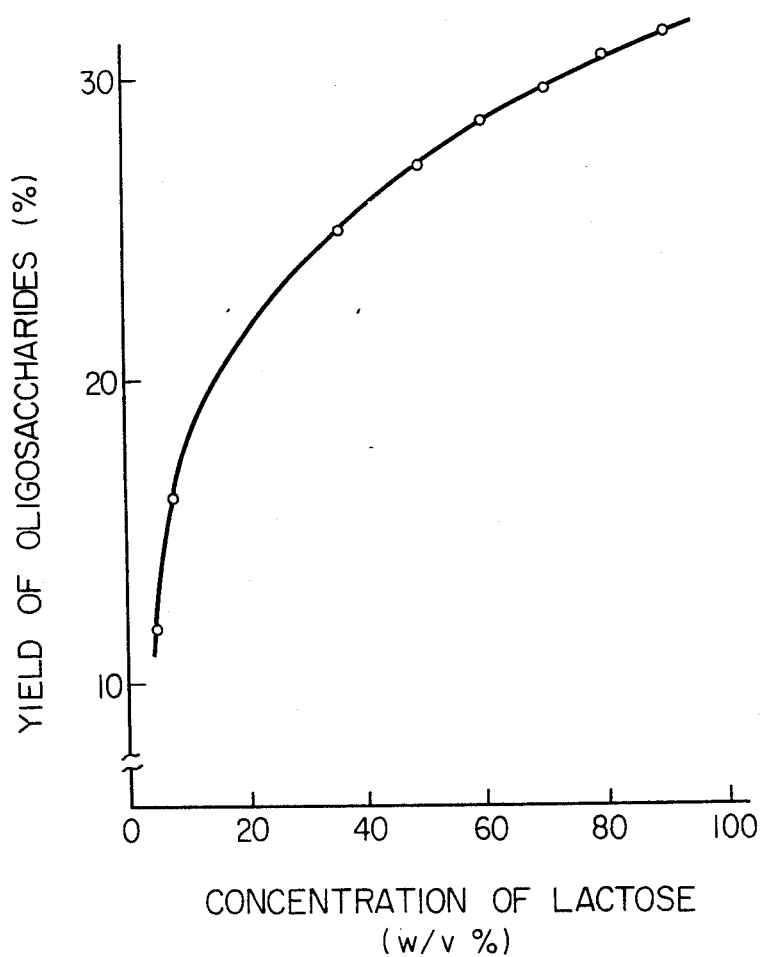
FIG. 2 shows the relationship between lactose concentration and the yield of "oligosaccharides"
Figure 3:
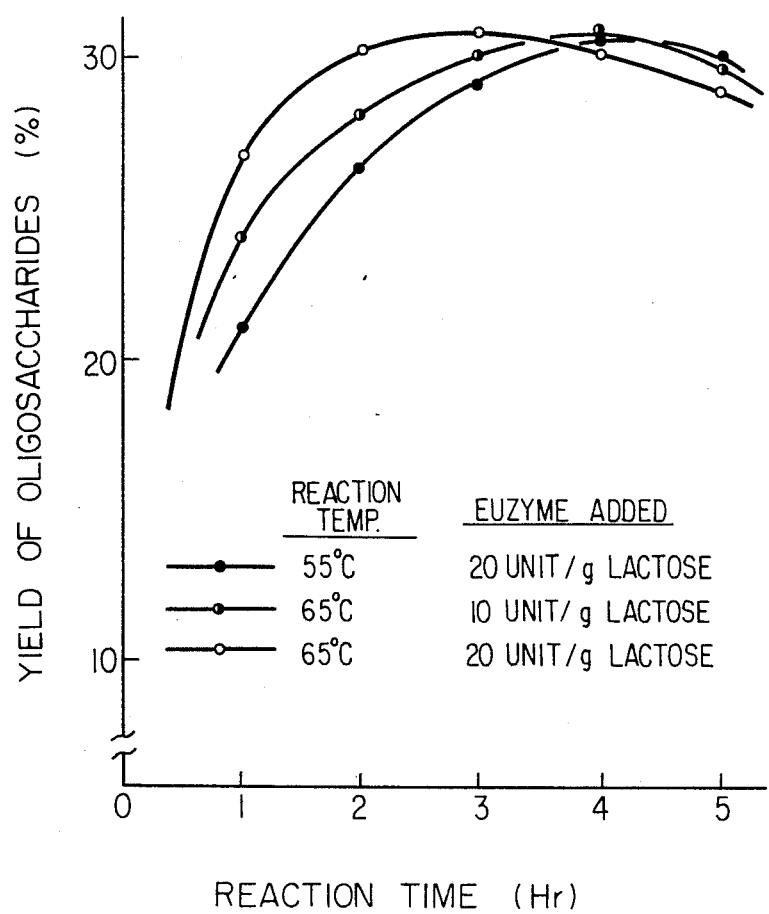
FIG. 3 shows the relationship between reaction time and the yield of "oligosaccharides" (lactose concentration in reaction mixture: 80% w/v).

Increases in the reaction temperature and the concentration of lactose not only enable an improvement in the utility of the reaction apparatus and a reduction in the concentrating cost of products, but also are effective for improving the yield of oligosaccharides (ratio of lactose converted into oligosaccharides), reducing the reaction time, and curtailing the amount of enzymes used. In other words, as shown in FIG. 2, the yield of oligosaccharides at the optimum reaction temperature increases as the concentration of lactose increases. In addition, as shown in FIG. 3, if the concentration of lactose is the same, the reaction time required for reaching the maximum yield for oligosaccharides decreases as the reaction temperature increases, and thus a less amount of enzyme is sufficient to the reaction. An amount of the enzyme is not specifically limited. However, even the amount of 10–20 units/g lactose can give a sufficient result.

In addition, when the reaction mixture is heated to inactivate the enzyme activity, if too-long a time is required, degradation of the oligosaccharides rapidly progresses during the heating, and it easily occurs to reduce in the yield of oligosaccharides. However, at a high reaction temperature, a short heating time is sufficient for the solution to reach the inactivation temperature of the enzyme, and thus stabilize the composition of the reaction product.

Considering the above-described facts, it is preferable that the concentration of lactose is as high as possible within the range of 50 to 90% (w/v), reaction temperature is maximum or near at which the enzyme can react at that concentration of lactose, and the reaction is stopped when the yield of oligosaccharides is at a maximum.

Other conditions of enzyme reaction, such as pH, may be the same as those of old production methods. In addition, crude lactose or substances containing high ratios of lactose, such as sweet whey powder (containing about 71% lactose) and desalted whey powder (containing about 75% lactose), other than high-purity lactose, can be used as raw material for the reaction.

The reaction product can be used as mixtures of sweetening sugars or foods and drinks which have proliferation accelerating functions for bifidobacteria as it is or, if necessary, after being subjected to decoloring purification concentration, drying, or other processing required for forming foods and drinks. It is a matter of course that the reaction product can be used for producing purified oligosaccharides, and high-purity oligosaccharides can be easily obtained because the reaction product contains small amounts of unreacted lactose and monosaccharides.

As can be seen from the above description, the present invention exhibits the following effects:
(1) It is possible to obtain a reaction product having a high content of oligosaccharides and a stable saccharide composition.
(2) Small amount of $\beta$-galactosidase is sufficient for the reaction.
(3) The utility of the production equipment is increased by the increase in the yield of "oligosaccharides".
(4) Small amount of heat energy is sufficient for concentrating the reaction mixture after the reaction has been completed.

The present invention is described below with reference to an example.

EXAMPLE 1

80g of edible-grade lactose and 48ml of water were mixed, and the mixture was heated under reflux in a boiling bath to obtain 100 ml of a 80% w/v lactose solution. This lactose solution is put in a hot-water bath at 65° C. so as to be cooled to the same temperature as that of the bath, and 800 units of $\beta$-galactosidase from *Aspergillus oryzae* (Lactase Y-400, produced by K. K. Yakult Honsha) which had been dissolved in 0.5 ml of water and warmed to be at 50° C.) were then added to the lactose solution. The thus-obtained mixture was allowed to react for 4 hours, and the reaction mixture was then heated at 90° C. for 20 minutes so that the enzyme was inactivated. When the sugar component of the reaction mixture was examined by high-pressure liquid chromatography, the contents of oligosaccharides, disaccharides, and monosaccharides were found to be 31%, 43% and 26%, respectively.

We claim:

1. A process of producing oligosaccharides of the formula: Gal—(Gal)$_n$—Glc, wherein Gal denotes a galactose residue, Glc represents a glucose residue and n is an integer of 1 to 4, comprising:
   reacting lactose at a concentration in a reaction mixture ranging from 50 to 90% (w/v) with $\beta$-galactosidase derived from *Aspergillus oryzae* at a reaction temperature ranging from 55° to 83° C.

2. The process according to claim 1, wherein the concentration of lactose is 60–85% (w/v).

3. The process according to claim 2, wherein the concentration of lactose is 70–80% (w/v).

4. The process according to claim 1, 2 or 3, wherein the reaction temperature is within the range of 60° C. to 80° C.

5. The process according to claim 4, wherein the reaction temperature is within the range of 62° C. to 75° C.

* * * * *